(12) United States Patent
Noguchi et al.

(10) Patent No.: US 7,449,181 B2
(45) Date of Patent: Nov. 11, 2008

(54) REMEDIES FOR CANCER

(75) Inventors: Toshihiro Noguchi, Ibaraki (JP); Akemi Baba, Oklahoma City, OK (US); Mitsuharu Hanada, Ibaraki (JP)

(73) Assignee: Sumitomo Pharmaceuticals Company Limited, Osaka-Shi (JP)

( * ) Notice: Subject to any disclaimer, the term of this patent is extended or adjusted under 35 U.S.C. 154(b) by 730 days.

(21) Appl. No.: 10/333,978

(22) PCT Filed: Jul. 26, 2001

(86) PCT No.: PCT/JP01/06467

§ 371 (c)(1),
(2), (4) Date: Apr. 21, 2003

(87) PCT Pub. No.: WO02/009754

PCT Pub. Date: Jul. 2, 2002

(65) Prior Publication Data

US 2003/0157097 A1 Aug. 21, 2003

(30) Foreign Application Priority Data

Jul. 28, 2000 (JP) .............................. 2000-228239

(51) Int. Cl.
*A61K 39/395* (2006.01)
*C05G 11/00* (2006.01)
*C07K 16/00* (2006.01)

(52) U.S. Cl. ................... 424/130.1; 536/16.8
(58) Field of Classification Search ...... 514/2; 424/130.1
See application file for complete search history.

(56) References Cited

U.S. PATENT DOCUMENTS 5,677,171 A * 10/1997 Hudziak et al. ............ 435/7.23
6,156,321 A * 12/2000 Thorpe et al. ............ 424/198.1
2003/0068318 A1* 4/2003 O'Brien et al. ........... 424/141.1

FOREIGN PATENT DOCUMENTS

JP 03-005397 B2 1/1991

OTHER PUBLICATIONS

Hida et al (Clinical Cancer Research, 2000, 2006-2011).*
Stancovski, et al (PNAS,USA, 88:8691-8695, 1991).*
Lewis, et al (Cancer Immunology Immunotherapy 37: 255-263, 1993).*
Strobel, et al (Gynecologic Oncology 73: 362-367, 1999).*
Karunagaran et al (EMBO J., 1996, 15:254-264).*
Graus-Porta et al (EMBO J., 1997, 16:1647-1655).*
Roitt et al, (Immunology, 1993, Mosby, St. Louis, p. 6.4-6.5).*
Winter et al (TIPS, 1993, 14:139-143).*
Pegram et al (J. Clin. Oncol., 1998, 16:2659-2671).*
Johns Hopkins Pathology Website—(http://ovariancancerjhmi.edu/recurrentqa.cfm).*
Glisson et al (Clinical Cancer Research, 2004, 20:944-946).*
Kim et al (Lung Cancer, 1998, 22:181-190).*
Kern et al (Cancer Research, 1990, 16:5184-5187), 88-91.*
Agus et al (Seminars in Oncology, 2000, 27:6:53-63.*
Pegram, M. et al. ONCOGENE, vol. 18, No. 13, pp. 2241-2251, Apr. 1999.
Perry, C. M. et al. BioDrugs, vol. 12, No. 2, pp. 129-135, Aug. 1999.
Ogawa, M., J. Cancer Res. Clin. Oncol., vol. 125, pp. 134-140, (1999).
Baselga et al., Cancer Research, vol. 58, pp. 2825-2831, (1998).
Noonberg et al., Drugs, vol. 59, No. 4, pp. 753-767, (2000).
Pegram, M. et al. Oncogene, vol. 18, No. 13, pp. 2241-2251, Apr. 1999.
Perry, C. M. et al. BioDrugs, vol. 12, No. 2, pp. 129-135, Aug. 1999.

* cited by examiner

*Primary Examiner*—Susan Ungar
(74) *Attorney, Agent, or Firm*—Birch Stewart Kolasch & Birch, LLP

(57) ABSTRACT

A medicament for treating cancer for use in combination therapy with an anti-HER2 antibody, which comprises amrubicin or a pharmaceutically acceptable salt thereof as an active ingredient.

6 Claims, No Drawings

REMEDIES FOR CANCER

This application is the national phase under 35 U.S.C. § 371 of PCT International Application No. PCT/JP01/06467 which has an International filing date of Jul. 26, 2001, which designated the United States of America.

TECHNICAL FIELD

The present invention relates to medicament for treating cancer for use in combined therapy with an anti-HER2 antibody, which comprises amrubicin or a pharmaceutically acceptable salt thereof as an active ingredient.

BACKGROUND ART

Amrubicin ((+)-(7S,9S)-9-acetyl-9-amino-7-[(2-deoxy-β-D-erythro-pentopyranosyl)oxy]-7,8,9,10-tetrahydro-6,11-dihydroxy-5,12-naphthacenedione) that is an anthracycline compound is known as an anti-cancer agent exhibiting less side effects in comparison with known anthracycline compounds such as doxorubicin and daunorubicin (Japanese Examined Patent Publication JP-B 3-5397).

Amrubicin is characterized by a stronger anti-cancer activity of its metabolite (amrubicinol: hydroxylated product at 13-position of the anthracycline skeleton) obtained by being readily reduced in vivo, than that of amrubicin itself. To the contrary, doxorubicin and daunorubicin do not have such characteristics (Cancer Chemother. Pharmacol., 30, 51–57 (1992)). In addition, cardiotoxicity of amrubicin was far less than that of doxorubicin in a rabbit chronic experimental model (Invest. New Drug; 15, 219–225 (1997)).

Although anthracycline anti-cancer agents have similar structures, diseases which are susceptible to treatment, modes of the action and the like have been known to vary as described below.

Daunorubicin and idarubicin are efficacious against leukemia, however, they are not efficacious against solid cancer. Doxorubicin, epirubicin, pirarubicin and aclarubicin have efficacies toward solid cancer (Nihon Iyakuhinshuu 23th. Ed., 2000, Yakugyou Jiho Co., Ltd.). Daunorubicin and doxorubicin inhibit DNA synthesis and RNA synthesis to the same extent, however, aclarubicin and marceromycin inhibit RNA synthesis to a greater extent than DNA synthesis, with mechanisms to exert anti-canser effects being entirely different each other (JJSHP 27, 1087–1110 (1991)). Although an inhibitory action for cell proliferation of daunorubicin and doxorubicin is attenuated upon reduction of the ketone at 13-position, idarubicin and its reduced form exhibit the action to a similar extent (Cancer Chemother. Pharmacol. 30, 51–57 (1992)). To the contrary, in regard to amrubicin, its reduced form exhibits the action which is stronger than amrubicin (Jpn. J. Cancer Res. 89, 1067–1073 (1998)). Tumor selectivity cannot be achieved by intravenous injection of doxorubicin, however, it was found that intravenous injection of amrubicin can result in the achievement of tumor selectivity in experiments on mouse (Jpn. J. Cancer Res. 89, 1061–1066 (1998)). An intercalation activity of doxorubicin is about ten times stronger than those of amrubicin and amrubicinol (Jpn. J. Cancer Res. 89, 1229–1238 (1998)). Although doxorubicin and daunorubicin largely distribute in cell nuclei, amrubicin and idarubicin largely distribute in cytoplasms (Ann. Haematol. 69, S13–S17 (1994); Jpn. J. Cancer Res. 89, 1229–1238 (1998); and Urol. Res. 25, 125–130 (1997)). Amrubicin and amrubicinol sufficiently stabilize a cleavable complex via topoisomerase II at a concentration which leads to 50% inhibition of cell proliferation, however, doxorubicin does not stabilize the cleavable complex at a concentration which leads to 50% inhibition of cell proliferation (Jpn. J. Cancer Res. 89, 1229–1238 (1998)).

Members in the anthracycline compounds thus vary in terms of their modes of action, and the indication therefor also vary. Among them, doxorubicin, and amrubicin and amrubicinol are extremely closely related in respect of chemical structures, however, the mechanisms of anti-cancer action are widely different.

Recently, an anti-cancer action by combined use of doxorubicin that is an anthracycline compound with Herceptin™ was reported, finding that the combination of doxorubicin with Herceptin™ showed additive effects in an in vitro experiment (M. Pegram et al., Oncogene, 18, 2241–2251 (1999)). However, when doxorubicin and Herceptin™ were used in combination, it was also reported that cardiotoxicity is developed at a high frequency in clinical use (a home page of Genentech, Ltd. on internet). Therefore, such a combination therapy was not always recognized as being effective. Herceptin™ is one of the antibodies directed against a human epidermal cell growth factor receptor 2 protein (hereinafter, referred to as HER2), which has been used as a remedy for breast cancer.

DISCLOSURE OF THE INVENTION

An object of the present invention is to provide a remedy for cancer by using amrubicin or a pharmaceutically acceptable salt thereof with an anti-HER2 antibody (for example, Herceptin™) in combination.

Aiming at improvement of an anti-cancer action of amrubicin, the present inventors have carried out investigation for combination effects with various medicines, and could achieve the desired effects by using in combination with Herceptin™. In other words, the present invention was accomplished through the finding that synergistic effects on a cancer cell strain can be achieved, accompanied with small influences on cardiotoxicity by using amrubicin with Herceptin™ in combination. When the present invention was compared with a combined therapy of doxorubicin with Herceptin™, merely additive effects have been found for doxorubicin as described above, and to the contrary, synergistic effects have been found according to the present invention. Moreover, doxorubicin results in cardiotoxicity at a high frequency through the use in combination with Herceptin™, and thus application in a clinical field is difficult. However, in accordance with the present invention, small influences on cardiotoxicity are exerted, leading to expectations as new a remedy for cancer. Difference of these effects between the present invention and doxorubicin is believed to be responsible for difference of modes of action of amrubicin and doxorubicin.

Summary of the present invention is as described below.

(1) A medicament for treating cancer for use in combination therapy with an anti-HER2 antibody, which comprises amrubicin or a pharmaceutically acceptable salt thereof as an active ingredient.

(2) The medicament according to (1) described above wherein said cancer is breast cancer, gastric cancer, renal cancer, salivary gland cancer, ovarian cancer, uterine body cancer or lung cancer.

(3) The medicament according to (1) or (2) described above wherein said cancer is a cancer in which HER2 is highly expressed.

(4) The medicament according to any one of (1) to (3) described above for administering amrubicin or a pharmaceutically acceptable salt thereof at 0.5–3.0 mg/kg/day when an anti-HER2 antibody is administered at 0.1–4.5 mg/kg/day.

(5) The medicament according to (4) described above for administering amrubicin or a pharmaceutically acceptable salt thereof on successive three days in every three weeks, while administering an anti-HER2 antibody every one week.

(6) The medicament according to any one of (1) to (3) described above for administering amrubicin or a pharmaceutically acceptable salt thereof at 1.5–9.0 mg/kg/day when an anti-HER2 antibody is administered at 0.1–4.5 mg/kg/day.

(7) The medicament according to (6) described above for administering amrubicin or a pharmaceutically acceptable salt thereof every three weeks, while administering an anti-HER2 antibody every one week.

(8) The medicament according to any one of (1) to (7) wherein a dosage ratio of amrubicin or a pharmaceutically acceptable salt thereof and an anti-HER2 antibody is 2:1–8:1 at one week after initiating the administration of both agents.

(9) Use of amrubicin or a pharmaceutically acceptable salt thereof for manufacturing a medicament for treating cancer which is administered in combination with an anti-HER2 antibody.

(10) The use according to (9) described above wherein said cancer is breast cancer, gastric cancer, renal cancer, salivary gland cancer, ovarian cancer, uterine body cancer or lung cancer.

(11) The use according to (9) or (10) described above wherein said cancer is a cancer in which HER2 is highly expressed.

(12) The use according to any one of (9) to (11) described above for administering amrubicin or a pharmaceutically acceptable salt thereof at 0.5–3.0 mg/kg/day when an anti-HER2 antibody is administered at 0.1–4.5 mg/kg/day.

(13) The use according to (12) described above for administering amrubicin or a pharmaceutically acceptable salt thereof on successive three days in every three weeks, while administering an anti-HER2 antibody every one week.

(14) The use according to any one of (9) to (11) described above for administering amrubicin or a pharmaceutically acceptable salt thereof at 1.5–9.0 mg/kg/day when an anti-HER2 antibody is administered at 0.1–4.5 mg/kg/day.

(15) The use according to (14) described above for administering amrubicin or a pharmaceutically acceptable salt thereof every three weeks, whist administering an anti-HER2 antibody every one week.

(16) The use according to anyone of (9) to (15) wherein a dosage ratio of amrubicin or a pharmaceutically acceptable salt thereof and an anti-HER2 antibody is 2:1–8:1 at one week after initiating the administration of both agents.

(17) A method of treating cancer comprising using an effective amount of an anti-HER2 antibody and an effective amount of amrubicin or a pharmaceutically acceptable salt thereof in combination.

(18) The method according to (17) described above wherein said cancer is breast cancer, gastric cancer, renal cancer, salivary gland cancer, ovarian cancer, uterine body cancer or lung cancer.

(19) The method according to (17) or (18) described above wherein said cancer is a cancer in which HER2 is highly expressed.

(20) The method according to any one of (17) to (19) described above comprising administering amrubicin or a pharmaceutically acceptable salt thereof at 0.5–3.0 mg/kg/day while administering an anti-HER2 antibody at 0.1–4.5 mg/kg/day.

(21) The method according to (20) described above comprising administering amrubicin or a pharmaceutically acceptable salt thereof on successive three days in every three weeks, while administering an anti-HER2 antibody every one week.

(22) The method according to any one of (17) to (19) described above comprising administering amrubicin or a pharmaceutically acceptable salt thereof at 1.5–9.0 mg/kg/day while administering an anti-HER2 antibody at 0.1–4.5 mg/kg/day.

(23) The method according to (22) described above comprising administering amrubicin or a pharmaceutically acceptable salt thereof every three weeks, while administering an anti-HER2 antibody every one week.

(24) The method according to any one of (17) to (23) wherein a dosage ratio of amrubicin or a pharmaceutically acceptable salt thereof and an anti-HER2 antibody is 2:1–8:1 at one week after initiating the administration of both agents.

(25) A kit for treating cancer comprising a first composition including amrubicin or a pharmaceutically acceptable salt thereof and a second composition including an anti-HER2 antibody.

(26) A medicament, use, method, kit or the like according to any one of (1) to (25) described above wherein Herceptin is used as said anti-HER2 antibody.

The medicament for treating cancer of the present invention comprises an effective amount of amrubicin, amrubicinol or a pharmaceutically acceptable salt thereof as an active ingredient, and is for use in combination with an effective amount of an anti-HER2 antibody.

The medicament for treating cancer of the present invention comprising an effective amount of amrubicin, amrubicinol or a pharmaceutically acceptable salt thereof as an active ingredient can enhance therapeutic effects on cancer of an anti-HER2 antibody by using it with anti-HER2 antibody in combination.

Exemplary pharmaceutically acceptable salt of amrubicin or amrubicinol may include acid addition salts and base addition salts. The acid addition salts include for example, inorganic acid salts such as hydrochloride, hydrobromide, sulfate, hydroiodide, nitrate, phosphate and the like; organic acid salts such as citrate, oxalate, acetate, formate, propionate, benzoate, trifluoroacetate, fumarate, maleate, tartrate, aspartate, glutamate, methanesulfonate, benzenesulfonate, camphorsulfonate and the like. The base addition salts include inorganic base salts such as sodium salt, potassium salt, calcium salt, magnesium salt, ammonium salt and the like; organic base salts such as triethylammonium salt, triethanolammonium salt, pyridinium salt, diisopropylammonium salt and the like.

The anti-HER2 antibody means an antibody against HER2 (human epidermal cell growth factor receptor 2 protein), which has a function inhibiting proliferation of cancer cells those are highly expressing HER2. The antibody may include a polyclonal antibody, a monoclonal antibody, a chimeric antibody, a humanized antibody and the like, which can be produced in accordance with a known process. For example, an anti-HER2 monoclonal antibody can be produced in accordance with a process described in WO89/06692. Further, an anti-HER2 humanized antibody can be produced in accordance with a process described in WO94/04679. Preferable examples of the anti-HER2 antibody include a humanized antibody, and specifically, Trastuzumab (Herceptin™, Genentech, Ltd.) is included.

Cancer which may be a therapeutic target in the present invention is not particularly limited, however cancer in which HER2 is highly expressed is preferred. For example, breast cancer, gastric cancer, renal cancer, salivary gland cancer, ovarian cancer, uterine body cancer, lung cancer and the like are included, and in particular, breast cancer is a preferable therapeutic target.

To a cancer patient, may be administered amrubicin or a pharmaceutically acceptable salt thereof in advance, may be administered an anti-HER2 antibody in advance, or may be administered both agent concurrently. When both are not concurrently administered, an interval between the administrations of both may be determined ad libitum.

In accordance with the present invention, since a synergistic effect is observed by using amrubicin with an anti-HER2 antibody in combination, a therapeutic effect on cancer can be achieved at a lower dosage than usual dosages of amrubicin or a pharmaceutically acceptable salt thereof and an anti-HER2 antibody. Therefore, in accordance with the present invention, side effects resulting from increased dosages of amrubicin or a pharmaceutically acceptable salt thereof and an anti-HER2 antibody can be minimized.

Amrubicin or a pharmaceutically acceptable salt thereof according to the present invention can be administered parenterally (for example, via intravenous, subcutaneous or intramuscular injection, or intravesically, topically, transrectally, transdermally or transnasally) in general. Preferably, intravenous injection can be exemplified. In addition, it can be also used for the oral administration, and forms for the oral administration may include for example, tablet, capsule, pill, granule, powder, liquid, syrup, suspension and the like.

Dose and administration frequency of amrubicin or a pharmaceutically acceptable salt thereof according to the present invention vary depending upon symptoms, age and body weight of the patient, mode of administration, and dose and administration frequency of the anti-HER2 which is used in combination. When administered as an injectable agent, it can be usually administered to an adult in the range of from about 10 mg to about 1000 mg, preferably from about 30 mg to about 500 mg per day, once or in divided doses for several times. When administered orally, it can be usually administered to an adult in the range of from about 100 mg to about 3000 mg, preferably from about 300 mg to about 1500 mg per day, once or in divided doses for several times. Furthermore, the administration can be repeated by providing intervals of from about one day to about 30 days.

The anti-HER2 antibody according to the present invention is usually administered to a targeted cancer cell site if possible, or alternatively, administered parenterally by an intravenous administration. In instances of the intravenous administration, it is preferably infused intravenously over about 30 minutes to about 90 minutes. For the parenteral administration, an anti-HER2 antibody is formulated into an injectable dosage form (solution, suspension or emulsion) together with a pharmaceutically acceptable excipient for the parenteral use. Such an excipient is essentially nontoxic and non-therapeutic. Examples of such an excipient include water, saline, Ringer solution, dextrose solution and 5% human serum albumin. Nonaqueous excipients such as nonvolatile oil, ethyl oleate and the like can be also used. The excipient can contain a substance for increasing isotonicity and chemical stability, for example buffer agents and stabilizers.

Dose and administration frequency of the anti-HER2 antibody according to the present invention depend upon symptoms, age and body weight of the patient, mode of administration, and dose and administration frequency of the amrubicin which is used in combination, however, it can be usually administered to an adult in the range of from about 5 mg to about 1000 mg, preferably from about 10 mg to about 300 mg per day, once or in divided doses for several times. Furthermore, the administration can be repeated by providing intervals of from about 5 days to about 10 days.

Preferred embodiments for exhibiting suppressive effects on cancer according to the present invention are explained below. For example, dosage ratio of amrubicin hydrochloride and Herceptin™ used in combination is preferably in the range of 2:1–8:1. Since amrubicin is readily converted into its active metabolite amrubicinol in vivo as demonstrated in Example 1, it is believed that the ratio of the concentration 2:1–8:1, which demonstrated synergistic effects when amrubicin and Herceptin™ were used in combination, reflects the dosage ratio of amrubicin hydrochloride and Herceptin™.

Also in the case of treating a cancer patient, the dosage ratio in the range of 2:1–8:1 is similarly preferred as a dosage ratio for the one week on the initiation of administration of amrubicin hydrochloride and Herceptin™.

Amrubicin hydrochloride is administered at a dosage of from about 1.5 to about 9.0 mg/kg for a single administration, or at a dosage of from about 0.5 to about 3.0 mg/kg on successive three days with repeating the administrations every three weeks. A route of administration is preferably intravenous administration. Herceptin™ is intravenously administered in the dosage range of from about 0.1 to about 4.5 mg/kg, which is administered every one week.

The administration of amrubicin hydrochloride and Herceptin™ follows one cycle of three weeks. The initiation of administration in each cycle is preferably executed on the same day. More specifically, in instances when amrubicin hydrochloride is administered on successive three days, it is preferred that amrubicin hydrochloride is administered on the first, second and third days of each cycle, while Herceptin™ is administered on the first, eighth and fifteenth days of the cycle.

The present invention also involves a kit for use in combination therapy of cancer comprising (a) a first composition including amrubicin or a pharmaceutically acceptable salt thereof as an active ingredient, and (b) a second composition including an anti-HER2 antibody as an active ingredient.

The fact that small influences on cardiotoxicity are exerted in combination use of amrubicin hydrochloride with Herceptin™ can be verified by a test in which a monkey that responds to Herceptin™ is used. More specifically, it can be verified by the observation that cardiotoxicity is strongly presented in a rhesus monkey when doxorubicin hydrochloride and Herceptin™ are intravenously administered, although cardiotoxicity is not presented even when the rhesus monkey is administered with amrubicin hydrochloride at a dosage of two times under the same condition. The administration of amrubicin hydrochloride at a dosage of two times of doxorubicin hydrochloride is carried out on the basis of therapeutic dosages of both agents.

EXAMPLES

The present invention is explained in more detail by way of examples below, and the present invention is not limited thereto.

[Experimental Process]

Method for Evaluation of Combination Effects in Vitro

Combination effects of amrubicin hydrochloride, amrubicinol hydrochloride and doxorubicin hydrochloride with Herceptin™ in vitro were examined using human breast cancer cells. The effects of the combined use were evaluated by calculating a Combination Index (CI) following a method of Pegram et al. (M. Pegram et al., Oncogene, 18, 2241–2251 (1999)).

Because amrubicinol is an active metabolite of amrubicin, it was added to the test agent. Amrubicinol can be produced by a method described in a literature (Ishizumi et al., J. Org. Chem., 52, 4477–4485 (1987)).

Human breast cancer cell line BT-474 (a cell line in which HER2 is highly expressed) was obtained from ATCC (American Type Culture Collection). In a medium comprising equal amount of D-MEM (Dulbecco's Modified Eagle Medium) medium and F-12 (Nutrient Mixture F-12) medium which further contains 2.5 mM L-glutamine, 10% bovine fetal serum (FCS) and 2.5 μg/ml amphotericin B, human breast cancer cell line BT-474 was subcultured. The culture was carried out in an incubator with 5% $CO_2$ at 37° C. This medium was also used in the following experiments.

Test agents were prepared as below.

Herceptin™ was dissolved in a dissolution solution attached thereto to prepare a 21 mg/ml stock solution. Thereafter, the solution was used after 2 fold serial dilutions with the medium.

Amrubicin hydrochloride and amrubicinol hydrochloride were dissolved in distilled water to give 1 mg/ml in use, which was used after sterilization by filtration followed by 2 fold serial dilutions with the medium.

Doxorubicin hydrochloride was obtained from Kyowa Hakko Kogyo Co., Ltd. A 2 mg/ml solution was prepared by adding 5 ml of sterile water to a 10 mg vial, and the solution was used.

Human breast cancer cell line BT-474 on subculture were subjected to a trypsin treatment, suspended in the medium, and seeded on a 96-well plate. The seeding density was set to be $1\times10^4$ cells/0.1 ml/well. After seeding, cells were cultured overnight in an incubator with 5% $CO_2$ at 37° C. (Day 0).

To the group for evaluating a single agent, were added 0.05 ml/well of a diluted solution of a test agent and 0.05 ml/well of the medium; and to the group for evaluating the combination effect, were added 0.05 ml/well of a diluted solution of a test agent and 0.05 ml/well of the diluted solution of Herceptin™ (Day 1). Final concentration of each agent was: 0.0625–16 μg/ml for amrubicin hydrochloride; 0.00625–1.6 μg/ml for amrubicinol hydrochloride; 0.00625–1.6 μg/ml for doxorubicin hydrochloride; 0.000781–0.4 μg/ml for Herceptin™. The experiments were conducted with n=3 for the agent-treated group, and with n=6 for the non-treated (control) group.

Until Day 4, culture was conducted in an incubator with 5% $CO_2$ at 37° C.

On Day 4, 0.02 ml of WST solution (a solution containing 1.3 mg/ml WST-1 (2-(4-iodophenyl)-3-(4-nitrophenyl)-5-(2, 4-disulfophenyl)-2H-tetrazolium, sodium salt) and 0.14 mg/ml 1-Methoxy PMS (1-Methoxy-5-methylphenazinium methylsulfate) in a phosphate buffer solution (PBS)) was added to each of the wells. Thereafter, culture was conducted in an incubator with 5% $CO_2$ at 37° C. for 2–4 hours. Absorbance of the culture was then measured with MICROPLATE READER Model 3550-UV (BioRad), and living cell number was measured.

Concentration D of amrubicin hydrochloride, amrubicinol hydrochloride, doxorubicin hydrochloride and Herceptin™ required for achieving a particular inhibition rate of proliferation (fa) was determined by the following formula (1). The concentration for the single agent was defined as $Df_1$ and $Df_2$, while the concentration when used in combination was defined as $D_1$ and $D_2$, and thus a Combination Index (CI) was calculated by the formula (2) (M. Pegram et al., Oncogene, 18, 2241–2251 (1999)).

$$fa=1-f$$

$$D=D_m \times \{fa/(1-fa)\}^{1/m} \quad (1)$$

$$CI=D_1/Df_1+D_2/Df_2+(D_1 \times D_2)/(Df_1 \times Df_2) \quad (2)$$

For a reference, f, $D_m$ and m were calculated as follows.

f=(mean value of absorbance at each of the agent concentrations)/(mean value of absorbance at the agent concentration of 0 mg/ml)

absorbance: $A_{420}$–$A_{630}$

Common logarithm of (1/f)−1 was plotted versus common logarithm of the agent concentration, and then a regression line was drawn in accordance with a least square method to find the slope and X intercept. The value of X intercept represents a common logarithm of an $IC_{50}$ value (concentration of the agent required for 50% inhibition of the cell proliferation). (As described above, $IC_{50}$ value was represented as $D_m$, and amrubicin hydrochloride, amrubicinol hydrochloride or doxorubicin hydrochloride is represented with the subscript 1 while Herceptin™ is represented with the subscript 2).

CI and inhibition rate of proliferation fa were calculated as described above. A CI value is obtained when the value of fa is 0.9. Evaluation is made as an additive effect at CI=1, as a synergistic effect at CI<1, and as an antagonistic effect at C>1.

Example 1

Combination Effects of Amrubicinol Hydrochloride and Doxorubicin Hydrochloride with Herceptin™

Using a method for evaluation of combination effects as described above, the combination effects were measured when a dosage ratio of amrubicinol hydrochloride and Herceptin™ is 2:1, and when a dosage ratio of doxorubicin hydrochloride and Herceptin™ is 2:1. The CI value was obtained when the value of fa is 0.9, which is shown in Table 1 below.

TABLE 1

|  | CI value | $D_1$ | $D_2$ | $Df_1$ | $Df_2$ |
| --- | --- | --- | --- | --- | --- |
| Present invention (Amrubicinol hydrochloride) | 0.38 | 0.239 | 0.119 | 0.671 | 6.312 |
| Control compound (Doxorubicin hydrochloride) | 0.92 | 0.373 | 0.187 | 0.434 | 6.312 |

Units for $D_1$, $D_2$, $Df_1$ and $Df_2$ are (μg/ml).

The results described above revealed that the combination effect with Herceptin™ was a synergistic effect in the case of the present amrubicinol hydrochloride because the CI value indicated a considerably lower value than 1.0. However, in the case of doxorubicin hydrochloride, an additive effect was suggested because the CI value indicated approximately 1.0, which did not suggest a synergistic effect. Thus, it was demonstrated that the effects by combined use with Herceptin™ greatly differ between amrubicinol hydrochloride and doxorubicin hydrochloride.

Example 2

Combination Effects and Dosage Ratio of Amrubicinol Hydrochloride with Herceptin™

Using a method for evaluation of combined use as described above, variation of the dosage ratio of amrubicinol hydrochloride and Herceptin™ was brought, and the evaluation test by the combined use in the range of 2:1–8:1 was conducted. A CI value was obtained when the value of fa is 0.9, which is shown in Table 2 below.

TABLE 2

| Dosage Ratio of Amrubicinol hydrochloride and Herceptin | CI value | $D_1$ | $D_2$ | $Df_1$ | $Df_2$ |
|---|---|---|---|---|---|
| 2:1 | 0.38 | 0.239 | 0.119 | 0.671 | 6.312 |
| 4:1 | 0.33 | 0.212 | 0.053 | 0.671 | 6.312 |
| 8:1 | 0.42 | 0.279 | 0.035 | 0.671 | 6.312 |

Units for $D_1$, $D_2$, $Df_1$ and $Df_2$ are (μg/ml).

As shown in Table 2 above, it was revealed that the combination of amrubicinol hydrochloride with Herceptin™ showed a synergistic effect, because the CI value showed lower values than 1.0 in either case in the range of 2:1–8:1 of the dosage ratio.

Example 3

Combination Effects of Amrubicin Hydrochloride with Herceptin™

Using a method for evaluation of combination as described above, the effect by combination of amrubicin hydrochloride and Herceptin™ was evaluated. The test for the effect by combination was conducted at a dosage ratio of 40:1 of amrubicin hydrochloride and Herceptin™. A CI value was obtained when the value of fa is 0.9, which is shown in Table 3 below.

TABLE 3

| | CI value | $D_1$ | $D_2$ | $Df_1$ | $Df_2$ |
|---|---|---|---|---|---|
| Present invention (Amrubicin hydrochloride) | 0.17 | 1.267 | 0.032 | 7.542 | 6.312 |

Units for $D_1$, $D_2$, $Df_1$ and $Df_2$ are (μg/ml).

As shown in Table 3 above, it was revealed that in the case of combination of amrubicin hydrochloride with Herceptin™, a synergistic effect was showed because the CI value showed a lower value than 1.0.

As described herein above, evaluation of the effect by combination was carried out by means of a Combination Index (CI) with a method for evaluation of combination by the Pegram method, and thus marked synergistic effects were found in combination of amrubicin hydrochloride with Herceptin™ and amrubicinol hydrochloride with Herceptin™.

Example 4

Cardiotoxicity Test Using Monkey

Presence of influences on cardiotoxicity is evaluated in an experiment using a rhesus monkey in the case of the combination of amrubicin hydrochloride with Herceptin™. More specifically, amrubicin hydrochloride and Herceptin™ are intravenously injected, and then the presence of cardiotoxicity is determined in a rhesus monkey administered with two times dose of amrubicin hydrochloride instead of doxorubicin hydrochloride under the following conditions in which cardiotoxicity is strongly presented.

Into vein of a rhesus monkey, is administered doxorubicin at a dose of 2.92 mg/kg (35 mg/m²), 7–8 times with three weeks intervals. On 140–150 days post initiation of the administration, vacuolation of myocardial cells are found upon histopathological observation of the heart (E. J. Gralla et al., Toxicology, 13, 263–273, 1979). Moreover, the administration of Herceptin™ to a human is carried out using a schedule of: administration at 4 mg/kg, followed by 2 mg/kg every week.

Accordingly, the agent-administered groups are set to be as follows:
1) agent non-administered group
2) doxorubicin hydrochloride 2–4 mg/kg, iv, 8q3W
3) doxorubicin hydrochloride 2–4 mg/kg, iv, 8q3W
   Herceptin™ 4 mg/kg, followed by 2 mg/kg every week, iv, administered 24 times
4) amrubicin hydrochloride 4–8 mg/kg, iv, 8q3W
5) amrubicin hydrochloride 4–8 mg/kg, iv, 8q3W
   Herceptin™ 4 mg/kg, followed by 2 mg/kg every week, iv, administered 24 times On 140–150 days post initiation of the administration, the animal is dissected, and histopathological diagnosis of the heart is carried out. Judging from the comparison of impairment of the myocardial cells, cardiotoxicity is evaluated.

INDUSTRIAL APPLICABILITY

According to the present invention, a medicament for combination therapy for cancer which is useful in treating a cancer patient is provided. More specifically, by using amrubicin hydrochloride with Herceptin™ in combination, synergistic anti-cancer effects can be achieved. Therefore, anti-cancer effects of amrubicin hydrochloride can be improved by using Herceptin™ in combination. Furthermore, the effects have come to be exerted also to a kind of cancer cells in which the effects of amrubicin hydrochloride are hard to be exerted, by using with Herceptin™ in combination. In addition, it becomes possible to suppress the dose of amrubicin hydrochloride on behalf of the synergistic effects by combination, thereby enabling cancer therapy with alleviated side effects to more extent.

The invention claimed is:

1. A method of treating breast cancer, which is a breast cancer in which HER2 is highly expressed, comprising administering an effective amount of trastuzumab and an effective amount of amrubicin or a pharmaceutically acceptable salt thereof in combination, whereby said breast cancer is treated.

2. The method according to claim 1, comprising administering amrubicin or a pharmaceutically acceptable salt thereof at 0.5–3.0 mg/kg/day while administering trastuzumab at 0.1–4.5 mg/kg/day.

3. The method according to claim 2, comprising administering amrubicin or a pharmaceutically acceptable salt thereof on successive three days in every three weeks, while administering trastuzumab every one week.

4. The method according to claim 1, comprising administering amrubicin or a pharmaceutically acceptable salt thereof at 1.5–9.0 mg/kg/day while administering trastuzumab at 0.1–4.5 mg/kg/day.

5. The method according to claim 4, comprising administering amrubicin or a pharmaceutically acceptable salt thereof every three weeks, while administering trastuzumab every one week.

6. The method according to any one of claims 1 and 2 to 5, wherein a dosage ratio of amrubicin or a pharmaceutically acceptable salt thereof and trastuzumab is 2:1–8:1 at one week after initiating the administration of both agents.

* * * * *